· US005618763A

United States Patent [19]
Frank et al.

[11] Patent Number: 5,618,763
[45] Date of Patent: Apr. 8, 1997

[54] ALKALI-ZINC-SILICATE GLASS-CERAMICS AND GLASSES

[75] Inventors: Martin Frank, Schaan; Susanne Wegner, Lindau; Volker Rheinberger, Vaduz; Wolfram Hoeland, Schaan, all of Germany

[73] Assignee: Ivoclar AG, Liechtenstein

[21] Appl. No.: 507,857

[22] Filed: Jul. 27, 1995

[30] Foreign Application Priority Data

Aug. 1, 1994 [DE] Germany ............ 44 28 839.5

[51] Int. Cl.$^6$ ............ C03C 14/00; A61K 6/02
[52] U.S. Cl. ............ 501/5; 501/6; 501/57; 501/63; 501/64; 501/69; 501/70; 501/72; 106/35; 65/33.1
[58] Field of Search ............ 106/35; 501/6, 501/5, 57, 69, 63, 64, 70, 72; 65/33.1

[56] References Cited

U.S. PATENT DOCUMENTS

| | | | |
|---|---|---|---|
| 3,772,132 | 11/1973 | Hara et al. ............ | 106/164 |
| 3,907,577 | 9/1975 | Kiefer et al. ............ | 106/37.7 |
| 3,954,487 | 5/1976 | Gliemeroth et al. ............ | 501/69 |
| 5,432,130 | 7/1995 | Rheinberger et al. ............ | 501/32 |

FOREIGN PATENT DOCUMENTS 1022681  3/1966  Germany .

OTHER PUBLICATIONS

Database WPI, Section Ch, Week 8112, Derwent Publications Ltd., London, GB, AN 81–20178D.

*Primary Examiner*—Melissa Bonner
*Attorney, Agent, or Firm*—Nixon, Hargrave, Devans & Doyle

[57] ABSTRACT

Alkali-zinc-silicate glass ceramics and glasses are described which have a linear thermal expansion coefficient in the range from 8.0 to $18.7 \times 10^{-6} K^{-1}$, an excellent chemical resistance and other advantageous optical properties and can be used in particular as dental material.

14 Claims, No Drawings

ALKALI-ZINC-SILICATE GLASS-CERAMICS AND GLASSES

The invention relates to alkali-zinc-silicate glass-ceramics and glasses and in particular to those which, because of their advantageous properties, such as linear thermal expansion coefficients adjustable in the range from 8.0 to $18.7 \times 10^{-6} K^{-1}$ and low processing temperatures, are suitable as dental material.

In dentistry, metallic dental restorations are usually veneered with ceramic layers in order to match the appearance of the restoration with that of the natural teeth. Such veneered restorations are also called veneer ceramics or metal ceramics. In order to avoid stresses between the metal base and the ceramic layer it is necessary to match the heat expansion coefficients of the ceramic materials to those of the metal.

It is known that leucite-containing glass ceramics have very high linear thermal expansion coefficients. These are to be attributed to the content of leucite which is formed from a suitable starting glass by controlled crystallization.

In order that a dental glass ceramic can be used for veneering the whole range of dental metals and alloys used, such as e.g. titanium up to alloys with a high gold content, it is necessary that its expansion coefficient is adjustable in a wide range. If, in addition, the dental glass ceramic is also to be used as correction material for sintered-on ceramics, then in particular low sintering temperatures of less than 880° C. and suitable optical properties, such as high translucence, are also very desirable.

Known glass ceramics and glasses frequently do not satisfy the requirement for thermal expansion coefficients adjustable in a wide range and for a low processing temperature. In addition, the known dental materials in many cases have components which are not completely safe from a physiological point of view, such as $Sb_2O_3$, or it is absolutely necessary to add $B_2O_3$ to them in order to achieve the properties desired for dental materials. According to the inventor's investigations on basic glasses of the $SiO_2$—$Al_2O_3$—$Na_2O$—$K_2O$ system, small $B_2O_3$ additions of about 3% by wt. lead to an unacceptable deterioration in chemical resistance and high $B_2O_3$ contents of about 12% by wt. to an expansion coefficient which is too low.

Dental ceramic materials containing $B_2O_3$ are e.g. known from DE-OS 39 11 460 and DE-PS 41 38 875. These materials have relatively low processing temperatures and can be used for veneering dental alloys. Their thermal expansion coefficient can however only be adjusted in the range from about 13 to $14 \times 10^{-6} K^{-1}$. The materials also necessarily contain $Sb_2O_3$, but no ZnO and no $ZrO_2$.

A ceramic material for veneering metallic dentures is also known from DE-OS 40 31 168. Even if it is reported that the expansion coefficient of this material is adjustable in a range from 8 to $17.5 \times 10^{-6} K^{-1}$, the material nevertheless contains 0.7 to 2.5% by wt. $B_2O_3$. Furthermore, no ZnO and no $ZrO_2$ are present in the material.

Porcelain compositions with a high $B_2O_3$ content of 7 to 33% by wt. and with processing temperatures in the region of 800° C. are known from U.S. Pat. No. 5,176,747. These compositions can be used as dental porcelain for veneering titanium or titanium alloys. The $B_2O_3$ used serves both to reduce the processing temperature and to reduce the thermal expansion coefficient. Moreover, an influence on the bond strength between metal substrate and ceramic is also attributed to the $B_2O_3$. Similar ceramic materials containing 8 to 17% by wt. $B_2O_3$ are described in EP-A-0 468 435. These materials contain no ZnO and can likewise be used for veneering dental restorations, such as crowns, bridges or prosthesis parts, which are produced from titanium or titanium alloys.

Further, leucite-containing glass ceramics are known from EP-A-0 155 564, which, however, contain $B_2O_3$ and $Sb_2O_3$ which is not safe from a physiological point of view.

It is the object of the invention to provide glass ceramics and glasses which can be processed at low temperatures by sintering, which have a linear thermal expansion coefficient adjustable in the range from in particular 8.0 to $18.7 \times 10^{-6} K^{-1}$, and which at the same time have advantageous optical properties, such as high translucence and opalescence, and an excellent chemical resistance and which can be produced without adding $B_2O_3$ and/or components which are not completely safe from a physiological viewpoint, and which are accordingly suitable in advantageous manner for use in dentistry.

This object is achieved by the alkali-zinc-silicate glass ceramic according to claims 1 to 7 and the alkali-zinc-silicate glass according to claim 10.

The subject-matter of the invention is also a process for preparing the glass ceramic, the use of the glass ceramic and of the glass and moulded dental products containing the glass ceramic and/or the glass.

The alkali-zinc-silicate glass ceramic according to the invention and also the alkali-zinc-silicate glass according to the invention are characterized in that they contain the following components:

| Component | % by wt. |
| --- | --- |
| $SiO_2$ | 52.0 to 63.5 |
| $Me(III)_2O_3$ | 8.5 to 13.0 |
| $K_2O$ | 0 to 20.5 |
| $Na_2O$ | 1.5 to 20.0 |
| $Li_2O$ | 0 to 5.0 |
| ZnO | 2.0 to 8.0, in particular 3.1 to 8.0 |
| Me(II)O | 2.5 to 6.5 |
| $TiO_2 + ZrO_2$ | 0.5 to 6.0 |
| $SnO_2$ | 0 to 9.5 |
| $P_2O_5$ | 0 to 4.0 |
| F | 0 to 2.0 | where a) the quantity of $Me(III)_2O_3$ given is formed from 0 to 13% by wt. $Al_2O_3$ and 0 to 9.5% by wt. $La_2O_3$; and b) the quantity of Me(II)O given is formed from 0 to 3.5% by wt. CaO, 0 to 4.5% by wt. BaO and 0 to 5.0% by wt. MgO.

Preferably, both the glass ceramic and the glass consist essentially of the aforementioned components.

There are preferred quantity ranges for some of the components of the glass ceramic and of the glass. These can be chosen independently of one another and are as follows:

| Component | % by wt. |
| --- | --- |
| $SiO_2$ | 52.0 to 61.0 |
| $Al_2O_3$ | 8.5 to 11.0 |
| $La_2O_3$ | 0 to 2.0 |
| $K_2O$ | 0 to 15.0 |
| $Na_2O$ | 6.0 to 15.0 |
| $Li_2O$ | 0 to 4.0 |
| ZnO | 3.6 to 7.0, in particular 4.0 to 7.0 |
| CaO | 0.5 to 3.5 |
| BaO | 1.0 to 4.5 |
| $TiO_2$ | 0 to 2.8 |
| $ZrO_2$ | 0.5 to 5.0 |
| $P_2O_5$ | 0 to 2.0 |

It is particularly preferred that the glass ceramic according to the invention and the glass according to the invention are essentially free from $B_2O_3$, antimony and/or lead compounds.

The glass according to the invention is preferably produced by melting suitable starting materials, such as carbonates, oxides and fluorides, at a temperature in the range from 1350° to 1650° C., preferably 1400° to 1600° C., over a period of 30 minutes to 4 hours, preferably one hour to 2.5 hours, with the formation of a homogeneous melt. The molten glass is then quenched in water, i.e. fritted, and the obtained glass granulate is ground up after drying.

The glass ceramic according to the invention is produced in particular by subjecting the obtained granulate of the glass according to the invention to a thermal treatment at a temperature in the range from 600° to 900° C. for a period of 30 minutes to 5 hours, preferably 30 minutes to 2 hours. Prior to the heat treatment the glass used is preferably ground to a powder with a grain size of less than 90 μm and sieved. The thermal treatment can also be effected by the heat treatments required when producing moulded dental products from the glass according to the invention, such as sintering steps.

It was established using scanning electron microscope investigations that the glasses according to the invention are free from crystals or have crystals only very occasionally. In contrast, the glass ceramics according to the invention contain crystals, in particular leucite crystals, which were formed by the controlled surface crystallization during the thermal treatment. The leucite crystals preferably form the main crystalline phase in the glass ceramics, and the average size of the leucite crystals is preferably less than 5 μm relative to the number of crystals.

In addition to leucite crystals, other crystalline phases can be formed depending on the chemical composition of the glass used. In addition to the different crystalline phases, microheterogeneous demixing regions, i.e. different glass phases, can also be present. These regions are recognizable through the scanning electron microscope as small microheterogeneous drop glass phases with a size of about 40 to 250 nm. The presence of this drop glass phase or of crystals influences the optical properties, such as opalescence and translucence, of the glass ceramics and glasses according to the invention.

The linear thermal expansion coefficient of the glass ceramics and glasses according to the invention can preferably be adjusted in the range from 8.0 to $18.7 \times 10^{-6} K^{-1}$, measured in the temperature range from 100° to 400° C. It is surprising that despite the high content of 52.5 to 63.5% by wt. $SiO_2$ and without the addition of $B_2O_3$, both high and low expansion coefficients can be imparted to the glass ceramics and glasses according to the invention. In contrast, according to the prior art an addition of $B_2O_3$ is in most cases absolutely necessary for achieving low expansion coefficients.

By using monovalent network modifier ions, such as potassium, sodium and lithium, and by using fluorine it was possible to reduce the processing temperature. Thus, the glasses and glass ceramics according to the invention can be sintered together in powder form at temperatures of preferably 640° to 850° C. and thus be processed.

The high ZnO content in the glass ceramics and glasses according to the invention contributes substantially to the good chemical resistance and reduces their viscosity compared with $ZrO_2$.

Moreover, ZnO is characterized by an excellent physiological compatibility.

In addition to the aforementioned components the glass ceramics and glasses according to the invention can also contain additives, such as dyestuffs, in particular colour pigments, oxides of the 3d-elements or metal colloids, or fluorescent agents, in particular ytterbium silicate doped with d- and f-elements. Other suitable additives for altering e.g. the optical and/or thermal properties of the glass ceramics and glasses according to the invention are other glasses, ceramics, other glass ceramics, opacifiers and/or stabilizers.

The glass ceramics and glasses according to the invention can be used either on their own as dental material or as constituents of dental materials, such as dental ceramic powders. The glass according to the invention and the glass ceramic according to the invention are in each case preferably used in the form of a powder having a particle size of in particular less than 90 μm. This glass ceramic or glass powder is suitable in particularly advantageous manner as correction material for metal ceramic or all-ceramic dental suprastructures, such as a partial crown, a crown or a bridge. For this purpose, the powder is applied on the desired sites of the dental suprastructure and sintered together in a vacuum furnace at temperatures from 640° to 850° C. The properties of the powder, such as thermal expansion coefficient and optical properties, can be matched to those of the sintered-on base material in question.

In another, preferred embodiment of the invention, the glass ceramic according to the invention can also be used in itself as covering or veneering material for all-ceramic or metallic dental suprastructures or those present in the form of alloys. For this, the powdered glass ceramic is mixed with water and applied onto the metallic or all-ceramic substrate. After moulding the desired dental restoration, such as bridge or crown, it is sintered at temperatures of 640° to 850° C. to give the finished, moulded dental product. It is of particular advantage that the thermal expansion coefficient of the glass ceramic can be varied within a wide range, and adjusted to $8.0 \times 10^{-6} K^{-1}$ for a titanium substrate and about $16.0 \times 10^{-6} K^{-1}$ for a substrate made from gold or alloy with a high gold content, and can thus be matched to the expansion coefficient of the substrate used.

It is particularly surprising that the glass ceramics and glasses according to the invention have a combination of low processing temperature, thermal expansion coefficients adjustable in a wide range and very good chemical resistance.

Coming into consideration as moulded dental products according to the invention, which contain the glass ceramic according to the invention or the glass according to the invention are in particular dental restorations, such as crowns, partial crowns and bridges.

The invention is further explained below with reference to examples.

EXAMPLES

Examples 1 to 21

A total of 21 different glass ceramics according to the invention and 21 different glasses according to the invention were produced. They had the chemical compositions given in Table I.

For some of the glass ceramics and glasses, selected properties are given in Table II, which had been determined on testpieces made from the corresponding glass or the corresponding glass ceramic. Further, in Table II under "Heat treatment" details are to be found of the starting material used in each case for the testpiece and information about any heat treatment of the starting material. All the starting materials for which no heat treatment is given were glasses according to the invention. The starting materials with given heat treatment were glass ceramics according to the invention. It is however to be borne in mind that in the case of the non-heat-treated glass no. 12, transformation to a corresponding glass ceramic took place when it was sintered in the temperature range given in Table II to give testpieces.

Table II further shows that as a rule a glass ceramic has a higher expansion coefficient than a glass of corresponding chemical composition.

The examples illustrate how glass ceramics and glasses with different properties can be obtained by altering the chemical composition and by a possible heat treatment.

TABLE I

|    | $SiO_2$ | $Al_2O_3$ | $La_2O_3$ | $K_2O$ | $Na_2O$ | $Li_2O$ | CaO | BaO | MgO | ZnO | $TiO_2$ | $ZrO_2$ | $SnO_2$ | $P_2O_5$ | F   | $CeO_2$ |
|----|---------|-----------|-----------|--------|---------|---------|-----|-----|-----|-----|---------|---------|---------|----------|-----|---------|
| 1  | 57.0    | —         | 9.4       | 13.8   | 6.4     | 1.7     | 1.8 | 4.0 | —   | 4.1 | —       | 1.0     | —       | —        | 0.8 | —       |
| 2  | 55.4    | 2.9       | 6.3       | 20.2   | 1.8     | 1.6     | 1.8 | 4.0 | —   | 4.0 | —       | 1.1     | —       | —        | 0.9 | —       |
| 3  | 53.7    | 2.9       | 6.3       | 13.5   | 6.3     | 1.6     | 1.9 | 4.0 | —   | 4.0 | —       | 1.0     | —       | 4.0      | 0.9 | —       |
| 4  | 58.3    | 9.7       | —         | 5.6    | 12.4    | 1.7     | 1.9 | 4.2 | —   | 4.2 | —       | 1.1     | —       | —        | 0.9 | —       |
| 5  | 54.5    | 10.0      | —         | —      | 20.0    | 2.5     | —   | —   | 5.0 | 4.0 | 1.0     | 1.0     | —       | —        | 2.0 | —       |
| 6  | 52.3    | 10.2      | —         | 8.7    | 9.6     | 2.6     | 1.3 | 3.7 | —   | 7.4 | 2.8     | 1.4     | —       | —        | —   | —       |
| 7  | 54.7    | 10.8      | —         | 9.2    | 9.3     | 2.4     | 1.4 | 3.9 | —   | 7.8 | —       | 0.5     | —       | —        | —   | —       |
| 8  | 57.0    | 10.4      | —         | 13.8   | 6.9     | 1.7     | 1.6 | 4.1 | —   | 3.1 | —       | 0.6     | —       | —        | 0.8 | —       |
| 9  | 56.6    | 9.6       | —         | 13.1   | 9.2     | —       | 1.9 | 4.1 | —   | 3.1 | 0.5     | 1.0     | —       | —        | 0.9 | —       |
| 10 | 60.3    | 10.0      | —         | 9.1    | 7.3     | 3.5     | 3.2 | 1.1 | —   | 4.4 | —       | 1.1     | —       | —        | —   | —       |
| 11 | 57.6    | 9.5       | —         | 10.1   | 7.0     | 4.2     | 1.9 | 4.1 | —   | 4.1 | 0.5     | 1.0     | —       | —        | —   | —       |
| 12 | 57.4    | 8.5       | 1.0       | 11.0   | 8.4     | 1.7     | 1.9 | 4.1 | —   | 4.1 | —       | 1.0     | —       | —        | 0.9 | —       |
| 13 | 57.5    | 9.6       | —         | 9.7    | 9.4     | 1.7     | 1.9 | 4.1 | —   | 4.2 | —       | 1.0     | —       | —        | 0.9 | —       |
| 14 | 56.0    | 8.4       | 1.0       | 10.9   | 8.3     | 1.6     | 1.8 | 4.1 | —   | 4.1 | —       | 1.4     | —       | 1.5      | 0.9 | —       |
| 15 | 56.5    | 9.4       | —         | 13.8   | 6.4     | 1.7     | 1.8 | 4.4 | —   | 4.1 | —       | 1.0     | —       | —        | 0.9 | —       |
| 16 | 63.3    | 10.5      | —         | —      | 9.2     | 4.9     | 0.9 | —   | 1.8 | 7.3 | —       | 1.1     | —       | —        | 1.0 | —       |
| 17 | 58.8    | 9.8       | —         | —      | 10.5    | 2.7     | 0.9 | —   | 1.7 | 4.2 | —       | 1.1     | 9.4     | —        | 0.9 | —       |
| 18 | 58.5    | 11.3      | —         | —      | 8.6     | 2.9     | 0.9 | —   | 1.7 | 4.2 | —       | 6.0     | 5.0     | —        | 0.9 | —       |
| 19 | 58.3    | 13.0      | —         | —      | 8.6     | 2.9     | 0.9 | —   | 1.7 | 4.2 | —       | 5.5     | 4.0     | —        | 0.9 | —       |
| 20 | 56.7    | 9.6       | —         | 12.8   | 9.2     | —       | 1.9 | 4.1 | —   | 3.6 | —       | 1.2     | —       | —        | 0.9 | —       |
| 21 | 56.0    | 9.4       | —         | 9.1    | 8.9     | 1.6     | 1.9 | 4.0 | —   | 4.1 | —       | 1.0     | —       | —        | 1.0 | 3.0     |

TABLE II

| Example No. | Heat Treatment | Sintering temperature range for producing rods for α-measurement | Lin. therm. expansion coefficient α $[10^{-6}K^{-1}]$ (100–400° C.) | Tg [°C.] | Resistance to acid [%] (material loss according to ISO 6872) | Optical behaviour |
|---|---|---|---|---|---|---|
| 1 | Glass powder <90 μm 750° C., 2 h | 710° C./690° C. | 12.1 | 461 | — | translucent |
| 2 | Glass powder <90 μm | 740° C./720° C. | 11.6 | 489 | 0.05 | very translucent |
| 3 | Glass powder <90 μm | 740° C./720° C. | 12.1 | 464 | 0.02 | very translucent |
| 4 | Glass powder <90 μm | 730° C./710° C. | 11.2 | 453 | 0.02 | very translucent |
| 6 | Glass powder <90 μm | 700° C./720° C. | 11.9 | 487 | 0.05 | — |
| 8 | Glass powder <90 μm | 700° C./720° C. | 11.5 | 460 | 0.04 | very translucent |
| 8 | Glass powder <90 μm 600° C., 60 min. | 700° C./720° C. | 14.0 | 430 | 0.04 | translucent |
| 9 | Glass powder <90 μm | 760° C./780° C. | 11.5 | 493 | 0.02 | very translucent |
| 10 | Glass powder <90 μm | 700° C./720° C. | 11.3 | 480 | 0.01 | very translucent |
| 12 | Glass powder <90 μm | 720° C./700° C. | 13.4 | 443 | 0.03 | very translucent |
| 12 | Glass powder <90 μm 750° C., 1 h | 720° C./740° C. | 16.2 | 431 | 0.02 | translucent |
| 13 | Glass powder <90 μm | 730° C./710° C. | 11.8 | 452 | 0.02 | very translucent |
| 13 | Glass powder <90 μm 750° C., 1 h | 710° C./690° C. | 14.7 | 437 | 0.03 | translucent |

TABLE II-continued

| Example No. | Heat Treatment | Sintering temperature range for producing rods for α-measurement | Lin. therm. expansion coefficient α $[10^{-6}K^{-1}]$ (100–400° C.) | Tg [°C.] | Resistance to acid [%] (material loss according to ISO 6872) | Optical behaviour |
| --- | --- | --- | --- | --- | --- | --- |
| 14 | Glass powder <90 μm | 740° C./720° C. | 12.1 | 454 | 0.02 | very translucent |
| 14 | Glass powder <90 μm 750° C., 1 h | 740° C./720° C. | 16.3 | 438 | 0.02 | translucent opal |
| 14 | Frit tempered 750° C., 1 h | 750° C. | 11.7 | 449 | 0.02 | very translucent, opal |
| 15 | Glass powder <90 μm 750° C., 30 min. | 750° C./730° C. | 18.7 | 408 | 0.05 | translucent |
| 17 | Glass powder <90 μm | 780° C./800° C. | 9.0 | 524 | 0.008 | translucent |

Example 22

This example describes the production of a glass ceramic according to the invention which can be used as a low-melting veneer ceramic or as correction material for both metal ceramics or ceramics.

Firstly, a starting glass with the chemical composition given in Table I for Example 12 was produced. For this, a mixture of oxides, carbonates and fluorides was melted at a temperature of 1550° to 1600° C. in a platinum/rhodium crucible over a homogenization time of about 2 hours. The glass melt was quenched in water and the formed glass frit was dried and ground up to a grain size of less than 90 μm. The obtained glass powder was then heat-treated for one hour at 750° C., again ground up and sieved to a particle size of less than 90 μm. Testpieces were produced using the obtained glass ceramic powder and the properties given in Table II under No. 12, with heat treatment, were determined.

To measure the linear thermal expansion coefficient, a rod-shaped green compact was produced from the glass ceramic powder, and fired in a vacuum furnace at a heat-up rate of 60° C./min and a holding time of 1 minute at a temperature of 720° C. Finally, it was fired without vacuum at an end-temperature of 740° C. and a holding time of 1 minute. The linear thermal expansion coefficient for the obtained testpiece was $16.2 \times 10^{-6}K^{-1}$, measured in the temperature range from 100° to 400° C. The expansion coefficient of this glass ceramic is thus matched to that of alloys with a high gold content.

It was also possible to sinter together the glass ceramic at a very low temperature of only 740° C. when producing small discs instead of rods. The production process for the small discs was that a green compact in the form of a small disc was formed from the glass ceramic powder and fired on a support coated with quartz powder in the vacuum furnace at 740° C. and with a holding time of one minute. The heat-up rate of the vacuum furnace was 60° C./min.

Determination of the chemical resistance of the glass ceramic by treating sintered small discs with 4% acetic acid in a Soxhlet apparatus in accordance with ISO 6872 led to a very small material loss of the glass ceramic of only 0.02%.

Because the linear thermal expansion coefficient is matched to alloys having a high gold content, and because of the very good chemical resistance and the low processing temperature, this glass ceramic is particularly suitable for sintering onto such alloys and as correction material for ceramics or metal ceramics.

To achieve linear thermal expansion coefficients which are matched to all gold-containing dental alloys customary at present, the glass ceramic can preferably be mixed with other powdered glass ceramics and glasses according to the invention having a chemical composition given in Table I.

Example 23

This example describes the production of a glass ceramic according to the invention which can be used as correction material for ceramics and in particular for metal ceramics.

Firstly, a glass having the composition given in Table I for Example 13 was melted and ground up in accordance with the procedure described in Example 22. The obtained powder was designated Powder I.

Further, a glass having the composition given in Table I for Example 14 was likewise melted and fritted in accordance with the procedure described in Example 22. The dried frit was then heat-treated for one hour at 750° C. and finally ground up in an agate mill and sieved to a particle size of less than 90 μm. The obtained powder was designated Powder II.

By suitably mixing these two powders with the glass ceramic powder according to Example 22 it was possible to adjust the expansion coefficient in the desired manner and thus to use the obtained mixture as correction material having very good optical properties for sintering on metal ceramic crowns. For example, a suitable mixture consisted of 70% by wt. Powder I, 15% by wt. Powder II and 15% by wt. powder according to Example 22, and this mixture had an expansion coefficient of $12.7 \times 10^{-6}K^{-1}$.

For use as correction material, this mixture was applied onto the site to be corrected of a metal ceramic crown, and the crown was fired at a temperature of 640° C., working under vacuum from 580° C. upwards. The heat-up rate was 60° C./min and the holding time was one minute. The finished crown was very translucent at the corrected site and, in particular in the cutting region, slightly opalescent, thereby producing a vivid effect.

At a temperature of 730° C. and with a holding time of a minute, it was possible to sinter together this mixture on quartz powder to give small discs. Moreover, small discs from this mixture produced and tested according to ISO 6872 showed a very good resistance to acid of only 0.02% material loss.

Example 24

This example describes a glass ceramic according to the invention which can be used as correction material for veneer ceramics and in particular for all-ceramic crowns.

Firstly, a glass having the chemical composition given in Table I for Example 15 was melted and ground according to the procedure described in Example 22. The obtained glass powder was then heat-treated for 30 minutes at 750° C. The properties of the obtained glass ceramic are given in Table II under No. 15.

By suitably mixing a powder of this glass ceramic with Powder I according to Example 23 it was possible to adjust the expansion coefficient such that the obtained mixture was useful as correction material for sintering onto all-ceramic crowns. A mixture suitable for this purpose contained 80% by wt. of the glass ceramic powder and 20% by wt. glass powder I according to Example 23 and had an expansion coefficient of $16.7 \times 10^{-6} K^{-1}$, measured in the range from 100° to 400° C.

Example 25

This example describes a glass according to the invention which has a linear thermal expansion coefficient of about $8.0 \times 10^{-6} K^{-1}$, measured in the range from 100° to 500° C., and which can accordingly be used for titanium alloys as veneering material or correction material. The glass has a processing temperature, i.e. a sintering temperature, of less than 880° C.

To produce it, a glass with the chemical composition given in Table I for Example 18 was melted and ground up according to the procedure given in Example 22. The testpieces were produced according to Example 22, although the firing temperature for producing the rod-shaped testpieces for the measurement of the expansion coefficient during the first firing was 850° C. and the second firing was carried out at 830° C. A thermal expansion coefficient of $8.1 \times 10^{-6} K^{-1}$, measured in the temperature range from 100° to 500° C. was determined for the thus-produced rod-shaped testpieces.

The firing temperature of small discs on quartz powder was only 850° C., and small discs made from the glass, produced and investigated in accordance with ISO 6872, showed a very good acid resistance of only 0.01% material loss. Moreover, small discs fired from the glass possessed a very high translucence.

We claim:

1. An alkali-zinc-silicate glass-ceramic, comprising the following components:

| Components | % by wt. |
| --- | --- |
| $SiO_2$ | 52.0 to 63.5 |
| $Me(III)_2O_3$ | 8.5 to 13.0 |
| $K_2O$ | 0 to 20.5 |
| $Na_2O$ | 1.5 to 20.0 |
| $Li_2O$ | 0 to 5.0 |
| ZnO | 3.6 to 8.0 |
| Me(II)O | 2.5 to 6.5 |
| $TiO_2 + ZrO_2$ | 0.5 to 6.0 |
| $SnO_2$ | 0 to 9.5 |
| $P_2O_5$ | 0 to 4.0 |
| F | 0 to 2.0 |
| $CeO_2$ | 0 to 3.0 | where a) $Me(III)_2O_3$ is formed from 0 to 13% by wt. $Al_2O_3$ and 0 to 9.5% by wt. $La_2O_3$; and b) Me(II)O is formed from 0 to 3.5% by wt. CaO, 0 to 4.5% by wt. BaO and 0 to 5.0% by wt. MgO.

2. The glass ceramic according to claim 1, comprising the following components, wherein the quantities of the components are, independently of one another, as follows:

| Component | % by wt. |
| --- | --- |
| $SiO_2$ | 52.0 to 61.0 |
| $Al_2O_3$ | 8.5 to 11.0 |
| $La_2O_3$ | 0 to 2.0 |
| $K_2O$ | 0 to 15.0 |
| $Na_2O$ | 6.0 to 15.0 |
| $Li_2O$ | 0 to 4.0 |
| ZnO | 3.6 to 7.0 |
| CaO | 0.5 to 3.5 |
| BaO | 1.0 to 4.5 |
| $TiO_2$ | 0 to 2.8 |
| $ZrO_2$ | 0.5 to 5.0 |
| $P_2O_5$ | 0 to 2.0 |

3. The glass ceramic according to claim 1, further comprising leucite crystals.

4. The glass ceramic according to claim 3, wherein the leucite crystals have an average size of less than 5 μm.

5. The glass ceramic according to claim 1, further comprising additive dyes, fluorescent agents, opacifiers, or stabilizers or glasses, ceramics, or glass ceramics beyond those present in the glass ceramic of claim 1.

6. The glass ceramic according to claim 1, wherein the glass ceramic has a linear thermal expansion coefficient of from 8.0 to $18.7 \times 10^{-6} K^{-1}$, measured in the temperature range of from 100° to 400° C.

7. A process for producing a glass ceramic having the following components:

| Components | % by wt. |
| --- | --- |
| $SiO_2$ | 52.0 to 63.5 |
| $Me(III)_2O_3$ | 8.5 to 13.0 |
| $K_2O$ | 0 to 20.5 |
| $Na_2O$ | 1.5 to 20.0 |
| $Li_2O$ | 0 to 5.0 |
| ZnO | 3.6 to 8.0 |
| Me(II)O | 2.5 to 6.5 |
| $TiO_2 + ZrO_2$ | 0.5 to 6.0 |
| $SnO_2$ | 0 to 9.5 |
| $P_2O_5$ | 0 to 4.0 |
| F | 0 to 2.0 |
| $CeO_2$ | 0 to 3.0 | where a) $Me(III)_2O_3$ is formed from 0 to 13% by wt. $Al_2O_3$ and 0 to 9.5% by wt. $La_2O_3$; and b) Me(II)O is formed from 0 to 3.5% by wt. CaO, 0 to 4.5% by wt. BaO and 0 to 5.0% by wt. MgO;

comprising producing a glass having the above composition; and subjecting the glass to a heat treatment at a temperature of from 600° to 900° C. from 30 minutes to 5 hours.

8. The process according to claim 7, wherein prior to the heat treatment, the glass is ground and sieved to give a powder with a grain size of less than 90 μm.

9. An alkali-zinc-silicate glass, comprising the following components:

| Components | % by wt. |
| --- | --- |
| $SiO_2$ | 52.0 to 63.5 |
| $Me(III)_2O_3$ | 8.5 to 13.0 |
| $K_2O$ | 0 to 20.5 |
| $Na_2O$ | 1.5 to 20.0 |
| $Li_2O$ | 0 to 5.0 |
| ZnO | 3.6 to 8.0 |
| Me(II)O | 2.5 to 6.5 |
| $TiO_2 + ZrO_2$ | 0.5 to 6.0 |
| $SnO_2$ | 0 to 9.5 |
| $P_2O_5$ | 0 to 4.0 |

-continued

| Components | % by wt. |
|---|---|
| F | 0 to 2.0 |
| $CeO_2$ | 0 to 3.0 | where a) Me $(III)_2O_3$ is formed from 0 to 13% by wt. $Al_2O_3$ and 0 to 9.5% by wt. $La_2O_3$;

b) Me(II)O is formed from 0 to 3.5% by wt. CaO, 0 to 4.5% by wt. BaO and 0 to 5.0% by wt. MgO; and c) the glass contains no $B_2O_3$.

10. A moulded dental product comprising the glass ceramic according to claim 1.

11. Dental material comprising the glass ceramic of claim 1.

12. Veneering material for all-ceramic or metallic dental superstructures comprising the glass ceramic of claim 1.

13. A moulded dental product comprising the glass according to claim 9.

14. Veneering material for all-ceramic or metallic dental superstructures comprising the glass of claim 9.

* * * * *